United States Patent [19]

Zimmerman et al.

[11] 4,264,576

[45] Apr. 28, 1981

[54] CONTRACEPTIVE METHODS AND COMPOSITIONS

[75] Inventors: Ronald E. Zimmerman, Danville; Philip J. Burck, Indianapolis; C. David Jones, Indianapolis; Arvind L. Thakkar, Indianapolis, all of Ind.

[73] Assignee: Eli Lilly and Company, Indianapolis, Ind.

[21] Appl. No.: 138,376

[22] Filed: Apr. 8, 1980

Related U.S. Application Data

[63] Continuation-in-part of Ser. No. 52,713, Jun. 28, 1979, abandoned, which is a continuation of Ser. No. 973,253, Dec. 26, 1978, abandoned.

[51] Int. Cl.³ .................... A61K 9/02; A61K 9/22; A61K 9/26; A61K 9/70
[52] U.S. Cl. ................... 424/22; 128/260; 424/19; 424/28
[58] Field of Search .................. 424/19–22, 424/28

[56] References Cited

U.S. PATENT DOCUMENTS

| | | | |
|---|---|---|---|
| 3,279,996 | 10/1966 | Long et al. | 424/32 |
| 3,545,439 | 12/1970 | Duncan | 128/260 |
| 3,888,975 | 6/1975 | Ramwell | 424/15 |
| 3,903,880 | 9/1975 | Higuchi et al. | 128/130 |
| 3,920,805 | 11/1975 | Roseman | 424/15 |
| 4,012,496 | 3/1977 | Schopflin et al. | 424/15 |
| 4,012,497 | 3/1977 | Schopflin | 424/15 |
| 4,014,987 | 3/1977 | Heller et al. | 424/15 |
| 4,016,251 | 4/1977 | Higuchi et al. | 424/15 |
| 4,034,749 | 7/1977 | Von Kesserv et al. | 128/130 |
| 4,053,580 | 10/1977 | Chien et al. | 424/15 |
| 4,067,961 | 1/1978 | Laughlin | 424/15 |

OTHER PUBLICATIONS

Mathews, M. B., J.A.C.S. 76:2948–2952 (1954) Testicular Hyaluronidase in Relation to Micelle Formation by Inactivating Agents.

Zanefield, L. "Sperm Enzyme Inhibitors As Antifertility Agents" Chap. 56: 570–582 of Human Semen and Fertility Regulation in Men, E. Hafez Ed. C. V. Mosby Co. St. Louis Mo. 1976.

"Barrier Methods" Population series H. No. 5 Sep. 1979 H-76 to H-118.

*Primary Examiner*—Shep K. Rose
*Attorney, Agent, or Firm*—James L. Rowe; Arthur R. Whale

[57] ABSTRACT

Introduction of a pharmaceutically acceptable non-toxic cation salt of a sulfoalkyl alkanoate, for example, sodium sulfopropyl dodecanoate, into the uterine lumen or vaginal cavity prevents conception.

4 Claims, No Drawings

CONTRACEPTIVE METHODS AND COMPOSITIONS

This is a continuation-in-part of application Ser. No. 52,713, filed June 28, 1979, now abandoned, which is a continuation of application Ser. No. 973,253, filed Dec. 26, 1978, now abandoned.

This invention relates to improved methods and compositions useful in human and veterinary medicine for the control of fertility.

Contraceptive methods involving the administration of chemical substances are widely practiced among women who desire to limit pregnancies. Such methods control fertility through various biological mechanisms. Among the presently used chemical methods of fertility control, the most important are those which act by means of the following: (a) suppression of ovulation through inhibition of gonadotropin release; (b) alteration of the female reproductive tract to prevent migration of sperm to the site of fertilization or, if fertilization occurs, to block implantation of the zygote (nidation); or (c) spermicidal action.

The oral contraceptives are the most prominent chemical contraceptive agents. These agents are of two types: (a) an estrogen combined with a progestin, and (b) a progestin alone. The contraceptives of the combined type act primarily by suppressing ovulation by negative feedback to prevent gonadotropin (LH and FSH) release by the hypothalamus, but alterations in the reproductive tract may also contribute to the antifertility effect. Such alterations include changes in the cervical mucus (which increase the difficulty of sperm migration) and in the endometrium (which decrease the likelihood of nidation). The action of a progestin alone in a very low oral dose (the "mini-pill") appears to involve primarily alterations in the female reproductive tract, but ovulation suppression may also occur. Although the oral contraceptives are highly effective, their use is associated with unpleasant side effects (such as nausea, depression, weight-gain, and headache) and an increased long-time risk of severe disease (such as thromboembolism, stroke, myocardial infarction, hepatic adenoma, gall bladder disease, and hypertension). Bleeding irregularities (such as break-through bleeding, spotting, and amenorrhea) are also frequent. A progestin, when administered alone, causes an increased incidence of changes in menstrual patterns, especially a marked increase in the amount and duration of menstrual bleeding.

Besides the oral route of administration a progestin alone may be administered systemically by various sustained-release dosage forms which include: (a) depo injection (IM) of an insoluble progestin (e.g. medroxy progesterone acetate), (b) a subdermal implant, or (c) an intravaginal insert. With these methods of administration, the progestin is absorbed into the body continuously at a very low daily dose, and the systemic effects are similar to those produced by oral administration of a progestin. However, as with the oral progestins, the sustained release methods may cause serious menstrual flow irregularities.

A recent method of contraception involves the sustained release of progesterone locally within the uterine lumen. In this method the progesterone is incorporated into a chamber within a flexible intrauterine device (IUD) formed from a polymer which is capable of releasing progesterone continuously into the uterine fluids at a slow rate over a prolonged period of time. The progesterone acts primarily locally to produce progestational alterations in the cervical mucus and endometrium. However, the antifertility action may also be caused by the reaction of the endometrium to the device itself ("IUD effect") or by systemic absorption of progesterone through the uterine membrane. Again, as with other progestin-only therapies, there is an increased incidence of menstrual flow irregularities. Another disadvantage of this method, is the increased risk of ectopic pregnancy.

Another recent development is the flexible IUD bearing metallic copper. The contraceptive action of this device results from the combined effects of the copper (which very slowly dissolves in the uterine fluids), which acts on the blastocyst and on the cervical mucus or endometrium, and of the IUD itself, which causes a foreign body reaction in the endomentrium.

Other chemical methods of contraception include the post coital administration of estrogens (e.g. diethylstilbestrol or ethynylestradiol) to prevent nidation or of prostaglandins which act as abortifacients. Both of these methods, at present, are limited to emergency situations. Still in the very early stages of development are immunological methods (vaccination) and methods involving the direct control of LHRH secretion from the pituitary by LHRH agonists or antagonists.

Another group of chemical contraceptive agents are the local spermatocides, such as nonoxynol or octoxynol, which are placed into the vagina immediately prior to coitus in the form of creams, foams, jellies, or suppositories. The spermicidal action takes place either in the vagina or elsewhere in the reproductive tract. For the latter to occur, the spermicidal agent is either absorbed on sperm membranes or is transported into the uterus under the influence of uterine contractions. The spermicidal methods are less reliable in preventing pregnancy and are inconvenient to use.

The intrauterine device (IUD) is the most common alternative to the oral contraceptives. The anti-fertility effect of the IUD is not caused by chemical activity. Instead the material forming the IUD induces a foreign body reaction (irritation) in the contiguous endomentrium which appears to interfere in some way with nidation. The use of the IUD is complicated, however, by serious problems including the possibility of intrauterine perforation, pelvic inflammation, discomfort, or aggravated menstrual periods.

From the foregoing, it is evident that the presently available methods of contraception are inadequate for various reasons because they: (a) may produce unpleasant side effects or increase the risk of serious disease, (b) may be unreliable, or (c) may be inconvenient and intrude on sexual enjoyment. Although many women practice contraception in spite of these inadequacies, a need exists in medicine for improved methods which combine effectiveness with increased safety and convenience. Such improvements are afforded by the present invention.

It has now been surprisingly found that a class of sulfoalkyl alkanoate salts (to be more fully described below) will effectively prevent fertilization when introduced in very small amounts in the female reproductive tract prior to coitus. The sulfoalkyl alkanoate salts, being non-steroidal, do not produce hormonal effects either locally or systemically, and, hence, they offer significant advantages over the oral contraceptive steroids and the sustained release progestin compositions heretofore used. The anti-fertility effect of the sulfopropyl alkanoate salts has been demonstrated in female rabbits using standard pharmacological test procedures whereby the test compound is introduced locally within the reproductive tract of the animal, the animal is then bred to a fertile buck, and the genital system of the animal is then examined to determine the number of embryos.

The sulfoalkyl alkanoate salts can be delivered satisfactorily within the female reproductive tract by slow release from silicone rubber compositions. Silicone rubber is known to be a useful vehicle for the sustained delivery of certain medicaments. Administration of a sulfoalkyl alkonate salt in the female reproductive tract by means of a sustained release silicone rubber composition will provide a more convenient and acceptable method of contraception than has heretofore been employed in the prior art.

The invention sought to be patented in its method of use aspects constitutes:

1. A method of contraception in a female mammal which comprises continuously introducing within the uterine lumen of said female, over a prolonged period of time at a controlled rate, an effective amount of a sulfoalkyl alkanoate salt of the formula

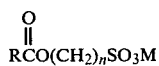
$$RCO(CH_2)_nSO_3M \qquad I$$

wherein R is a straight chain alkyl group having from 9 to 13 carbon atoms, a branched chain alkyl group having from 9 to 17 carbon atoms, or an alkenyl group having from 9 to 13 carbon atoms; n is 2, 3 or 4; and M is a pharmaceutically acceptable, non-toxic cation.

2. A method of contraception in a female mammal which comprises continuously introducing within the vaginal cavity of said female, over a prolonged period of time at a controlled rate, an effective amount of a sulfoalkyl alkanoate salt of the formula

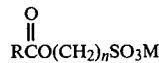
$$RCO(CH_2)_nSO_3M \qquad I$$

wherein R is a straight chain alkyl group having from 9 to 13 carbon atoms, a branched chain alkyl group having from 9 to 17 carbon atoms, or an alkenyl group having from 9 to 13 carbon atoms; n is 2, 3 or 4; and M is a pharmaceutically acceptable, non-toxic cation, whereby said sulfoalkyl alkanoate salt is transported into the uterine fluids with sperm during or after coitus; or 3. A method of contraception in a female mammal which comprises introducing into the vaginal cavity immediately before coitus an effective amount of a sulfoalkyl alkanoate salt of the formula

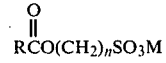
$$RCO(CH_2)_nSO_3M \qquad I$$

wherein R is a straight chain alkyl group having from 9 to 13 carbon atoms; a branched chain alkyl group having from 9 to 17 carbon atoms, or an alkenyl group having from 9 to 13 carbon atoms; n is 2, 3 or 4; and M is a pharmaceutically acceptable non-toxic cation, whereby said sulfoalkyl alkanoate salt is transported into the uterine fluids with sperm during or after coitus.

In its composition aspects, the present invention contemplates:

1. A contraceptive composition suitable for insertion and comfortable retention in the uterine lumen which comprises: (a) about 1 to about 40 percent by weight of a sulfoalkyl alkanoate salt of the formula

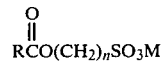
$$RCO(CH_2)_nSO_3M \qquad I$$

wherein R is a straight chain alkyl group having from 9 to 13 carbon atoms, a branched alkyl group having from 9 to 17 carbon atoms, or an alkenyl group having from 9 to 13 carbon atoms; n is 2, 3 or 4; and M is a pharmaceutically acceptable, non-toxic cation; and (b) about 60 to about 99 percent by weight of a biocompatible, bioinsoluble, flexible silicone rubber carrier matrix, said matrix being capable of continuously releasing said sulfoalkyl alkanoate salt into the uterine fluids at a controlled rate over a prolonged period of time; or 2. A contraceptive composition suitable for insertion and comfortable retention in the vaginal cavity which comprises: (a) about 1 to about 40 percent by weight of a sulfoalkyl alkanoate salt of the formula

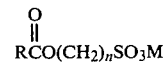
$$RCO(CH_2)_nSO_3M \qquad I$$

wherein R is a straight chain alkyl group having from 9 to 13 carbon atoms, a branched chain alkyl group having from 9 to 17 carbon atoms, or an alkenyl group having from 9 to 13 carbon atoms; n is 2, 3 or 4; and M is a pharmaceutically acceptable, non-toxic cation; and (b) about 60 to about 99 percent by weight of a biocompatible, bioinsoluble, flexible silicone rubber carrier matrix, said matrix being capable of continuously releasing said sulfoalkyl alkanoate salt into the vaginal fluids at a controlled rate over a prolonged period of time; or 3. A contraceptive foam, jelly, cream, suppository, or sponge composition suitable for comfortable insertion into the vaginal cavity immediately prior to coitus which comprises: (a) an effective amount of a sulfoalkyl alkanoate salt of the formula

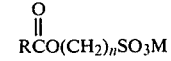
$$RCO(CH_2)_nSO_3M \qquad I$$

wherein R is a straight chain alkyl group having from 9 to 13 carbon atoms; a branched chain alkyl group having from 9 to 17 carbon atoms, or an alkenyl group having from 9 to 17 carbon atoms; n is 2, 3 or 4; and M is a pharmaceutically acceptable, non-toxic cation; and (b) a pharmaceutically acceptable, non-toxic vaginal excipient.

In the sulfopropyl alkanoate salts of Formula I, M is a pharmaceutically acceptable non-toxic cation (e.g. sodium, potassium lithium, calcium, magnesium, copper, aluminum, zinc, pyridinium, substituted pyridinium, ammonium, or substituted ammonium). Sodium is preferred. It will be appreciated by those skilled in the art that when the cation (M) has a valency greater than one, more than one alkyl sulfate moiety will be associated with the cation. The sodium sulfoalkyl alkanoates of Formula I, when n is 3 or 4, are prepared by reacting an appropriate sodium alkanoate ($RCO_2Na$) with propane sultone or butane sultone in an inert organic solvent according to the procedure of T. Hikota, *Bulletin of the Chemical Society of Japan*, 43, 2236 (1970). The compounds of Formula I, wherein n is 2, are prepared by treating an alkanoic acid chloride (RCOCl) with sodium isethionate also by the procedure of Hikota supra. The alkanoic acids employed as starting materials, and the sodium salts thereof, are either known compounds or can be prepared from known compounds by methods well known in the art.

By the term "alkenyl" is meant a straight chain or branched chain unsaturated hydrocarbon group containing one double bond, which may be oriented in the cis or trans configuration, provided that the double bond cannot be in the terminal position.

Examples of straight chain alkanoate compounds useful for the purpose of this invention are:

sodium sulfopropyl decanoate (R is $C_9$ alkyl; n is 3; M is sodium);

sodium sulfopropyl undecanoate (R is $C_{10}$ alkyl; n is 3; M is sodium);

sodium sulfopropyl dodecanoate (R is $C_{11}$ alkyl; n is 3; M is sodium);

sodium sulfopropyl tridecanoate (R is $C_{12}$ alkyl; n is 3; M is sodium); and sodium sulfopropyl tetradeconate (R is $C_{13}$ alkyl; n is 3; M is sodium);

sodium sulfoethyl dodecanoate (R is $C_{11}$ alkyl; n is 2; M is sodium).

When R is a branched chain alkyl group, the preferred alkyl groups are those which have the formula:

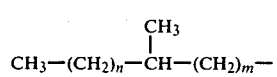

wherein n and m are, independently, an integer from 0 to 14, provided that n+m must be no less than 6 or no greater than 14. Examples of branched chain alkanoate compounds useful for the purpose of this invention are:

sodium sulfopropyl 12-methyltridecanoate (R is

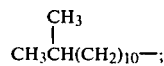

n is 3; M is sodium);

sodium sulfopropyl 15-methylheptadecanoate (R is

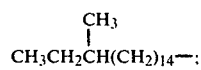

n is 3; M is sodium);

sodium sulfopropyl 16-methylheptadecanoate (R is

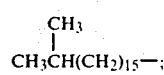

n is 3; M is sodium);

When R is an alkenyl group, the preferred alkenyl groups are those having a straight hydrocarbon chain of the formula

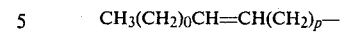

wherein 0 and p are, independently, an integer from 0 to 10, provided that n+m must be no less than 6 or no greater than 10. Examples of straight chain alkenoate compounds useful for the purpose of this invention are:

sodium sulfopropyl myristoleate (R is cis-$CH_3(CH_2)_3CH=CH(CH_2)_7$—, n is 3; M is sodium)

sodium sulfopropyl myristelaidate (R is trans-$CH_3(CH_2)_3CH=CH$—$(CH_2)_7$—; n is 3; M is sodium).

The sulfoalkyl alkanoate salts represented by Formula I control fertility by inhibiting an enzyme which is required during fertilization to allow sperm to penetrate the outer investments of the ovum. An ovum contains three outer investments—the cumulus oophorus, the corona radiata, and the zona pellucida—which are barriers to fertilization. In the male and when first deposited in the female, sperm is incapable of fertilizing an ovum since it lacks the capacity to penetrate the outer investments. Before fertilization can occur, specific hydrolytic enzymes emanating from the sperm must digest each investment so as to form a passage for sperm penetration. The process by which sperm active the ability to penetrate the ovum is known as "capacitation". Capacitation involves the labilization of sperm membranes and the release, activation, or exposure of the ovum penetrating enzymes as needed to attack each investment. There is evidence that the activation of the ovum penetrating enzymes may involve the removal of specific inhibitors of the enzymes. The exact biochemical transformations occurring during capacitation are not fully understood, but the enzymes must exert their action either while bound to the sperm membranes or upon release from sperm after the sperm and the ovum make contact in the fallopian tube. For a review of the biochemistry of capacitation and of the inhibition of ovum penetrating enzymes, see McRorie et al., *Am. Rev. Biochem.*, 43, 777 (1974) and E. S. Hafez, Ed., "Human Semen and Fertility Regulation in Men", C. V. Mosby Co., St. Louis, Mo., 1976, pages 201 to 242 and 563 to 582.

It has been found that the alkylsulfo alkanoate salts of Formula I inhibit in vitro the action of hyaluronidase, a sperm acrosomal enzyme known to be responsible in vivo for the penetration of the cumulus oophorus by causing degradation of hyaluronic acid which occurs between the cells of the cumulus oophorus. Inhibition of this enzyme in vivo will lead to interruption of the ovum penetration process thereby effectively preventing fertilization and pregnancy. Certain compounds of Formula I also have been found to inhibit in vitro the action of acrosin, a sperm acrosomal enzyme known to be responsible in vivo for the penetration of the zona pellucida by causing degradation of the glycoproteins of the zona pellucida. The compounds having anti-acrosin activity are: sodium sulfopropyl 15-methylheptadecanoate, sodium sulfopropyl 16-methylheptadeconate, sodium sulfopropyl myristoleate, and sodium sulfopropyl myristelaidate.

The ability of the sulfopropyl alkanoate salts to prevent digestion of the cumulus oophorus has been demonstrated in in vitro tests wherein an isolated ovum from a rabbit is observed under a microscope while being incubated in calcium-free Ringer's solution in the presence of testicular hyaluronidase with and without the sulfopropyl alkanoate salt being present in the medium. In the absence of sodium sulfopropyl dodecanoate, complete removal of the cumulus oophorus is observed. With the compound present, the cumulus oophorus remain substantially intact.

In order to prevent pregnancy, an effective, amount of the sulfoalkyl alkanoate salt must be present at the site of fertilization in the fallopian tube when sperm and the ovum make contact prior to penetration of the ovum. The sulfoalkyl alkanoate sulfate salt can be administered by introduction locally either within the uterine lumen or vaginal cavity. By both modes of administration, the sulfoalkyl alkanoate salt is carried to the site of fertilization either by adsorbtion onto sperm membranes or by transport through the fluids of the reproductive tract. In uterine fluids, the sulfoalkyl alkanoate salt reaches the fallopian tube by means of diffusion or active transport. In vaginal fluids, the compound passes to the uterine fluids either adsorbed on sperm membranes or by active transport under the influence of uterine contractions. The preferred method of administration from the stand point of convenience to the female user is to introduce the sulfoalkyl alkanoate salt continuously within the uterus or vagina during the fertile period of the female (i.e. the period three to four days after ovulation when an ovum is present in the fallopian tube). By this method an effective amount of the active compound is present within the reproductive tract each day to prevent fertilization if coitus should occur during the fertile period. Such a method would be independent of the sex act and would avoid the inconvenience of repeated independent dosages.

The continuous administration of the active compound can be accomplished effectively by incorporating it into an organopolysiloxane (silicone rubber) composition and placing said composition into the uterine lumen or vaginal cavity. The active compound is slowly introduced into the uterine or vaginal fluids by release from the silicone rubber at a controlled rate, an effective amount of the compound being present continuously in such fluids. The silicone rubber acts as an insoluble carrier matrix for supporting the active compound while it is being introduced into the uterine or vaginal fluids. Silicone rubber is bioinsoluble and biocompatible (i.e. it is non-toxic, insoluble, and physiologically inert when in contact with body tissues and fluids) and is flexible enough to avoid uterine perforation and to prevent or mimimize an IUD effect on the contiguous endometrium. The silicone rubber carrier can be formed in any shape or size suitable for insertion and comfortable retention in the uterine lumen or vaginal cavity. For example, for intrauterine use it can be in the form of a Lippes loop, butterfly, coil, Birnberg bow, or T configuration, or modifications thereof, which configurations are well known in the art to be useful for retention in the uterus. [See, for example, U.S. Pat. Nos. 3,234,938; 3,533,406; 3,935,860; 3,077,879; 3,250,271; and 3,319,625.] For intravaginal use, it can be formed as a flexible ring, similar in configuration to that of the retaining ring of a diaphragm, which is known in the art to be useful for retention in the vagina. [See, U.S. Pat. Nos. 3,545,439 and 3,920,805.]

Organopolysiloxanes are described in U.S. Pat. No. 3,279,996 (Long et al), the disclosure of which is incorporated herein by reference. This patent describes implants for releasing a drug in the tissues of living organisms comprising the drug enclosed in a capsule formed of silicone rubber or the drug dispersed in a prosthesis made from silicone rubber. A number of biocompatible insoluble silicone rubbers are described in the Long et al. patent. A preferred silicone rubber is dimethylpolysiloxane which is curable at room temperature or above with an appropriate curing agent. Suitable dimethylpolysiloxane rubbers are sold commercially as liquid elastomers which are mixed with a curing agent to obtain the solid rubber. Among such commercially available rubbers are those sold by Dow-Corning Corporation identified as Silastic 382 and MDX-4-4210. Such rubbers consist of two components, a first component comprising liquid uncured rubber, and a second component comprising a curing agent. The two components are mixed and the mixture is allowed to cure. Heating can be employed to enhance curing, if desired. Another suitable type of dimethylpolysiloxane rubber is a high consistency medical grade elastomer such as that sold by Dow-Corning Corporation under the designation MDF-0198. For preparing carrier compositions suitable for intrauterine or intravaginal use, the active compound, preferably in a very fine particle size, in the amount desired is thoroughly mixed mechanically with the uncured dimethylpolysiloxane rubber. The curing agent is then added, and the mixture is placed, e.g. by injection, in a mold having a cavity of the desired size and shape. The elastomer is allowed to cure at an appropriate temperature and time. Upon completion of the curing, the molded composition is removed at room temperature. Using the above described procedure there is obtained a dimethylpolysiloxane in which the active compound is uniformly dispersed. When in contact with the body fluids in which the compound is soluble (i.e. the uterine or vaginal fluids), the compound is released into the fluids.

It will be recognized by those skilled in the art that the silicone rubber compositions useful for the purposes of this invention can also be made by other methods which are conventional in the art. One method is to form a silicone rubber composition containing the dispersed active compound, using the molding technique described above, and then to coat the composition with a very thin layer of silicone rubber. For example, formed silicone rubber rods containing dispersed active compound can be coated with silicone rubber using conventional coating, bonding, or laminating techniques, such as by immersing the rods in a solution of uncured silicone rubber in a volatile solvent, removing the rod, evaporating the solvent, and curing the coating of silicone rubber formed thereby by heating. Alternatively, the rod containing the dispersed active compound can be fitted tightly inside a very thin hollow silicone rubber tube and the ends can be sealed. If desired, the silicone rubber composition containing the active compound can be coated with, or enclosed tightly within, a microporous material through which the compound can pass by microporous flow, when the finished composition is bathed in vaginal or uterine fluids. The microporous material can be a microporous silicone rubber or other microporous polymer, the choice and use of which will be apparent to those skilled in the art.

Another method of making the compositions is by coating silicone rubber containing the dispersed active compound on an inert, biocompatible, insoluble, flexible core material. Preferably, the inert core is formed from silicone rubber, but other conventional suitable materials can be used.

It will also be understood that an effective amount of the active contraceptive compound can be releasably affixed to the outer surface of the silicone rubber composition, so that when the composition is inserted into the uterus or vagina, there is an immediate release of the compound into the body fluids. The compound can be deposited or coated on the medicated silicone rubber compositions using conventional methods.

It will be apparent to those skilled in the art that, if desired, an effect amount of an X-ray contrast agent (e.g. barium sulfate) can be included in the compositions of the invention in order to render the compositions opaque to X-rays. It will also be apparent that, if desired, a non-toxic pharmaceutically acceptable filler can be added to the silicone rubber. The use of such fillers are well known in the art.

In general, the concentration of the active compound in the silicone rubber carrier composition may vary from about 1 to about 40 percent by weight. A preferred range is from about 5 to about 20 percent. A concentration of about 10 percent has been found to be most preferred.

The rate of release of the active compound can be assessed by an in vitro test wherein the medicated carrier is placed in fresh water or fresh calcium-free Ringer's solution at 37° for sucessive periods of time (e.g. 24 hours), and the amount of active ingredient released after each period is assayed from a determination of the acrosin inhibiting activity of the solution. For intrauterine use, a release rate equivalent to from about 1 to about 200 µg. of the active compound per day is desired. A rate from about 50 to about 150 µg. per day is preferred. For intravaginal use, a release rate of about 1 to about 5 mg. per day is desired.

It is desirable that the rate of delivery be substantially constant over the period in which the carrier composition is present in the uterine lumen or vaginal cavity. The duration of drug delivery should cover at least the fertile period of the female. Of course, for maximum convenience to the female, the delivery should extend over a prolonged period of time, preferably with intrauterine use one year or more, since this will avoid the inconvenience of repeated removal and reinsertion of the medicated carrier. For intravaginal use, the carrier composition is preferably removed at the start of the menstrual period and is reinserted after bleeding stops.

For administration to females, who for personal reasons do not wish to use a sustained release medicated intrauterine or intravaginal composition, an alternative method of administration of the active compound is by means of a pharmaceutically acceptable jelly, foam, cream, or suppository, which is inserted into the vagina immediately prior to coitus in a manner similar to that employed for administering spermicidal compositions. [See the article entitled "Spermicides", *Population Reports:* Series H, Vol. 7, No. 5, Sept. 1979; published by Population Information Program, The Johns Hopkins University, Baltimore, Md.] The jelly, foam, cream, or suppository acts as a vehicle for carrying an effective amount of the active ingredient into the vaginal fluids from where it is carried into the uterus by adsorption on sperm membranes or by active transport. The active ingredient can be compounded into vaginal jellies, foams, creams, or suppositories according to procedures which are conventional in the art, by employing the usual excipients (buffer, emulsifier, preservatives, and the like), the choice and amount of which will be apparent to those skilled in the art.

For reasons of convenience, esthetics, or more precise control of dosage, a vaginal suppository is preferred. The suppository composition must be chemically and physically stable under conditions of storage and handling, and also must be capable of melting and/or dissolving when inserted in the vagina to effect satisfactory release of the active compound into the vaginal fluids. A preferred suppository composition comprises an effective amount of the active compound in a suitable polyethylene glycol vehicle. Various polyethylene glycols, either alone or in combination, are known in the art to be useful for making vaginal suppository compositions, and the choice of a particular vehicle will be apparent to those skilled in the art.

For intravaginal use, an effective amount of the active compound can be absorbed into a biocompatible, bioinsoluble, non-toxic sponge-like soft polymer, which when inserted and retained in the vagina will release the compound by desorption into the vaginal fluids. The sponge can be allowed to remain in the vagina during coitus or it can be removed prior to coitus. Suitable polymers for this use are well known in the art, for example, a hydrophilic polymer, such as polymeric 2-hydroxyethyl methacrylate which, if desired, may contain a cross-linking agent (e.g. dimethacrylate).

The following examples illustrate the methods and compositions of the present invention.

EXAMPLE 1

Hyaluronidase Inhibition In Vitro

The inhibition of hyaluronidase is assessed using chondroitin sulfate as the enzyme substrate according to the following procedure:

Agar plates containing chondroitin sulfate (0.1 percent) are prepared by the following method: water solutions of 1 percent agarose, 2 M sodium chloride (0.1 vol.), 1 M sodium acetate (pH 5.0, 0.1 vol), and sodium azide (0.5 mg./ml., 0.1 vol.) are mixed and the mixture is brought to the boiling temperature. After cooling to about 65° C., a solution of chondroitin sulfate (10 mgl./ml., 0.1 vol.) is added. After cooling to about 45° C., the resulting mixture (20 ml.) is poured onto a petri dish. The plates are allowed to cool to room temperature. A well 2 mm. in diameter is then cut in the agar surface. Testicular bovine hyaluronidase (Sigma Chemical Company) (5 µl., 10 mg/ml.) and a solution of the test compound (5 µl., 10, 5, 2, 1.3 or 1.0 mg/ml) in 1 M sodium acetate buffer, pH 5.0, are added to the well. A control using only the buffer solution without added test compound is also run. The plates are then incubated overnight (about 16 hours) at 37° C. The zones of hydrolysis of chondroitin sulfate by hyaluronidase are visualized by flooding the plate with 10 percent cetyl trimethyl ammonium bromide. The area of the zone is logarithmically proportional to the concentration of hyaluronidase. Inhibitor activity is determined by comparing the area of hydrolysis from the test compound to the area of hydrolysis from the control. The results are expressed as percent inhibition calculated as follows:

$$\text{Percent inhibition} = 100 - 100 \times \frac{\text{Area of zone of inhibition for test compound}}{\text{Area of zone of inhibition for control}}$$

When tested according to the above described method the sodium sulfopropyl alkanoates of Formula I gave the following results:

TABLE I

In vitro hyaluronidase inhibition of sodium sulfoalkyl alkanoate

| Compound or Formula I R | n | Concentration (mg/ml) | Inhibition (%/mg) |
|---|---|---|---|
| $CH_3(CH_2)_8$ | 3 | 10 | 90 |
|  |  | 5 | 36 |
|  |  | 2 | 13 |
|  |  | 1.3 | 0 |
| $CH_3(CH_2)_{10}$ | 3 | 10 | 100 |
|  |  | 5 | 100 |
|  |  | 2 | 34 |
|  |  | 1.3 | 0 |
|  |  | 1.0 | 13 |
| $CH_3(CH_2)_{11}$ | 3 | 10 | 100 |
|  |  | 5 | 87 |
|  |  | 2 | 75 |
|  |  | 1.3 | 18 |
| $CH_3(CH_2)_{12}-$ | 3 | 10 | 100 |
|  |  | 5 | 31 |
|  |  | 2 | 26 |
|  |  | 1.3 | 16 |
| $\underset{|}{CH_3}$<br>$CH_3CH(CH_2)_{10}-$ | 3 | 1.0 | 14 |
| $\underset{|}{CH_3}$<br>$CH_3CH(CH_2)_{14}-$ | 3 | 1.0 | 13 |
| $\underset{|}{CH_3}$<br>$CH_3CH_2CH(CH_2)_{13}-$ | 3 | 1.0 | 13 |
| cis- $CH_3(CH_2)_3-$<br>$CH=CH(CH_2)_7-$ | 3 | 1.0 | 13 |
| trans- $CH_3(CH_2)_3-$<br>$CH=CH(CH_2)_7-$ | 3 | 1.0 | 13 |
| $CH_3(CH_2)_{10}-$ | 2 | 1.0 | 38 |

EXAMPLE 2

Preparation of Medicated Dimethylpolysiloxane Rubber Composition

In a suitable container there are mixed 2430 mg. of dimethylpolysiloxane elastomer (Dow-Corning MDX-4-4210), 270 mg. of curing agent (Dow-Corning MDX-4-4210) and 300 mg. of sodium sulfopropyl n-dodecanoate. After mixing, the mixture is placed in a 3 ml. syringe (no needle) and injected into a stainless steel mold block, containing two cylindrical mold cavities. The block is placed in a vacuum oven at 90° C. (slight vacuum) for about 1 hour. Upon cooling (after about 10 to 15 minutes) the molded compositions are removed to give 2 rods 3 mm. in diameter and 63 mm. in length. The content of sodium sulfopropyl n-dodecanoate in each composition is 10% (W/W). Following the same procedure but using 2565 mg. of elastomer, 285 mg. of curing agent, and 150 mg. of sodium sulfopropyl n-dodecanoate there is obtained dimethylpolysiloxane compositions containing 5% of active ingredient.

EXAMPLE 3

Determination of drug release rate from dimethylpolysiloxane rubber compositions An appropriate sample of a dimethylpolysiloxane rubber composition in which is incorporated the test compound is placed in a suitable amount of calcium-free Ringers solution, and the sample and solution are incubated together at 37° C. for a period of time (e.g. 24 hours). The solution is removed and assayed for hyaluronidase inhibition (expressed as percent inhibition) using the technique described in Example 1. The equivalent amount of test compound in the removed solution is calculated from standard inhibition curves in which hyaluronidase inhibition is plotted against concentration of the test compound. The calculated result are expressed as micrograms of test compound released per day.

The above test may be repeated for an extended period of time, for example, for 1 day to 360 days, or more, by adding fresh calcium-free Ringer's solution after each removal of the solution for assay.

Samples of a dimethylpolysiloxane rubber composition containing 10% W/W of sodium sulfopropyl n-dodecanoate were tested as above described for 14 days. The sample weight was 4 mg. and the amount of added solution was 1 ml. After the 14th day, the release rate from the samples averaged 1-3 micrograms/day.

EXAMPLE 4

Antifertility effects, in vivo

A. By intrauterine administration

Dutch Belted virgin rabbits, each weighing 3-4 pounds, are randomly selected and anesthetized with sodium pentobarbital (50 µg./ml.) administered by IV drip. The uterus of each animal is exposed and a 40-mg. sample in the shape of a rod (3 mm. in diameter) of dimethylpolysiloxane rubber (as prepared in Example 3) containing 10% W/W of sodium sulfopropyl n-dodecanoate is sutured into the right uterine horn at a random location in between the cervix and the uterotubal junction. The left horn is left untreated to serve as control. The rubber rod is placed into the uterine horn by passing a curved needle through it and through the uterine wall pulling the rod into the uterine lumen. The entry is closed by suturing. Animals (blank) are similarly treated using unmedicated dimethylpolysiloxane rubber to serve as a second group of controls. The animals are given 300,000 units of Duracillin ® per day (in four doses) and are allowed to recover for 14 days. Each animal is bred to a male of proven fertility and is immediately given a dose (IV) of appropoximately 100 units of human chorionic gonadotropin (HCG) to facilitate ovulation. Fourteen days after breeding, the animal are sacrificed by cervical dislocation and the uterine horns are examined for implanted embryos. The number of embryos per uterine horn are recorded.

A comparison of implanted embryos in untreated horns, in blank horns, and in treated horns is set forth below in Table II.

TABLE II

Inhibition of fertilization by sodium sulfopropyl n-dodecanoate slowly released in the uterus

| Treatment | No. of Uterine horns | Total No. of embryos | $\frac{Embryos}{Horn}$ (x + S.D.) |
|---|---|---|---|
| Untreated | 32 | 52 | 1.6 ± 0.7 |
| Blank | 13 | 14 | 1.1 ± 0.2 |
| Sodium sulfo-<br>propyl decanoate | 11 | 1 | 0.09** |

*Release rate from dimethylpolysiloxane, 1–3 mg./day, in vitro (Calc. on basis of hyaluronidase inhibition).
**p < .001 compared to untreated; p < .001 compared to blank.

It should be noted that in the blank animals the number of embryos per horn is smaller. This is because the sutured material decreases the available area for implant of the fertilized ova. However the difference between the number of embryos in the untreated and in the blank animals is not satistically significant.

B. By intravaginal administration

Equal volumes of Ky-jelly ® and either Ca++ free Ringer's solution or a 10 mg./ml. solution of the compound to be tested in Ca++ free Ringer's solution are well mixed. One milliliter of this is placed into the vagina of a virgin dutch belted female rabbit using a syringe. The female is then immediately bred to a fertile buck. The female is injected I.V. with 100 units of human chorionic gonadotrophin to assure a good ovulation rate.

After approximately 14 days the females are sacrificed by cervical dislocation and the genital system examined for the number of embryos.

When tested as above described, sodium sulfopropyl n-dodecanoate gave the results shown below in Table III:

TABLE III

Inhibition of fertilization by sodium sulfopropyl n-dodecanoate in female rabbits by intravaginal administration

| Treatment | No. of animals | No. of embryos | Avg. No. of Embryos per animal |
|---|---|---|---|
| control | 4 | 31 | 7.7 |
| treated | 6 | 0 | 0 |

EXAMPLE 5

Removal of cumulus oophorus from ova, in vitro

Female rabbits are given 100 units of pregnant mares serum (PMS), IM, and 134 units of HCG, IV. After 13 hours the animals are sacrificed, and the ovaries are excised. The ovaries are submerged in calcium-free Ringer's solution containing 20% rabbit serum which had been heated to 55° C. for 20 minutes. Ova with cumulus intact are removed and placed in calcium-free Ringer's solution for incubation at 37° C. Hyaluronidase (10 μl.) of a 10 mg./ml. solution in calciumfree Ringer's solution is added to 20 ova in 1 ml. of the incubation medium. To 10 ova in the same medium is added 10 μl. of a solution of sodium sulfopropyl n-dodecanoate (10 mg./ml.) in calcium-free Ringer's solution. To 10 other ova in the same media is added 10 μl. of calcium-free Ringer's solution as control. The mixtures are incubated at 37° C., and the cumulus oophorus is examined at 15 minute intervals with an American Optical stereomicroscope. In the absence of sodium sulfopropyl n-dodecanoate, the cumulus oophorus is completely removed. With sodium sulfopropyl n-dodecanoate the cumulus remains substantially intact.

What is claimed is:

1. A contraceptive composition suitable for insertion and comfortable retention in the uterine lumen which comprises: (a) about 1 to about 40 percent by weight of a sulfoalkyl alkanoate salt of the formula

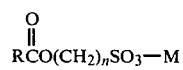

$$R\overset{O}{\overset{\|}{C}}O(CH_2)_nSO_3{-}M$$

wherein R is a straight-chain alkyl group having from 9 to 13 carbon atoms, a branched chain alkyl group having from 9 to 17 carbon atoms, or an alkenyl group having from 9 to 13 carbon atoms; n is 2, 3 or 4; and M is a pharmaceutically acceptable, non-toxic cation and (b) about 60 to about 99 percent by weight of a biocompatible, bioinsoluble, flexible silicone rubber carrier matrix, said matrix being capable of continuously releasing said sulfoalkyl alkanoate salt into the uterine fluids at a controlled rate over a prolonged period of time.

2. A composition as defined in claim 1 wherein the silicone rubber is dimethylpolysiloxane.

3. A composition as defined in claim 1 or 2, wherein the sulfoalkyl alkanoate is:
 sulfopropyl n-decanoate,
 sulfopropyl n-dodecanoate,
 sulfopropyl n-tridecanoate,
 sulfopropyl n-tetradecanoate,
 sulfopropyl 15-methylheptadecanoate,
 sulfopropyl 16-methylheptadecanoate,
 sulfopropyl myristoleate,
 sulfopropyl myristelaidate,
 sulfopropyl 12-methyltridecanoate, or
 sulfoethyl n-dodecanoate.

4. A composition as defined in claim 3 wherein the cation is sodium.

* * * * *